US00PP18260P2

(12) United States Plant Patent
Schräder

(10) Patent No.: US PP18,260 P2
(45) Date of Patent: Nov. 27, 2007

(54) **NEW GUINEA *IMPATIENS* PLANT NAMED 'GRUNEU 25'**

(50) Latin Name: *Impatiens hawkeri*
Varietal Denomination: GrüNeu 25

(75) Inventor: Ralf Schräder, Lüdinghausen (DE)

(73) Assignee: Gruenewald Veredelings B.V., MN's-Gravenzande (NL)

( * ) Notice: Subject to any disclaimer, the term of this patent is extended or adjusted under 35 U.S.C. 154(b) by 0 days.

(21) Appl. No.: 11/480,099

(22) Filed: Jun. 30, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—S. B. McCormick-Ewoldt
(74) *Attorney, Agent, or Firm*—The Webb Law Firm

(57) ABSTRACT

'GrüNeu 25' is a new variety of New Guinea *Impatiens* that exhibits large, salmon-rose colored flowers.

1 Drawing Sheet

Botanical classification: *Impatiens hawkeri.*
Varietal denomination: 'GrüNeu 25'.

BACKGROUND OF THE INVENTION

The present invention comprises a new and distinct cultivar of *Impatiens hawkeri* known by the varietal name 'GrüNeu 25'. The new variety was discovered in The Netherlands. The new variety is a result of cross breeding Seedling #2-15 (female parent) (unpatented) and Seedling #2-07 (male parent) (unpatented). The purpose of the breeding program was to develop a cultivar that exhibited large flowers. The new variety is similar in growth habit to its parents, but differs in flower color, size and quantity. The new variety was first asexually reproduced by vegetative propagation by cutting in The Netherlands. The new variety has been trial and field tested and has been found to retain its distinctive characteristics and remain true to type through successive asexual propagations. Characteristics that distinguish the new variety from others known to the breeder include:

Flower color;

Flower size;

Growing habit; and

Flower quantity.

The new variety was grown in a 11–19 cm container in The Netherlands. The new variety initiates roots in 8 days at 16° C. A rooted plant is produced in 21 days at an average temperature of 16–21° C. Its rooting habit is round and freely branching.

DESCRIPTION OF THE DRAWING

The accompanying photographic drawing illustrates the new variety, with the color being as nearly true as is possible with color illustrations of this type.

DESCRIPTION OF THE PLANT

Figure 1:
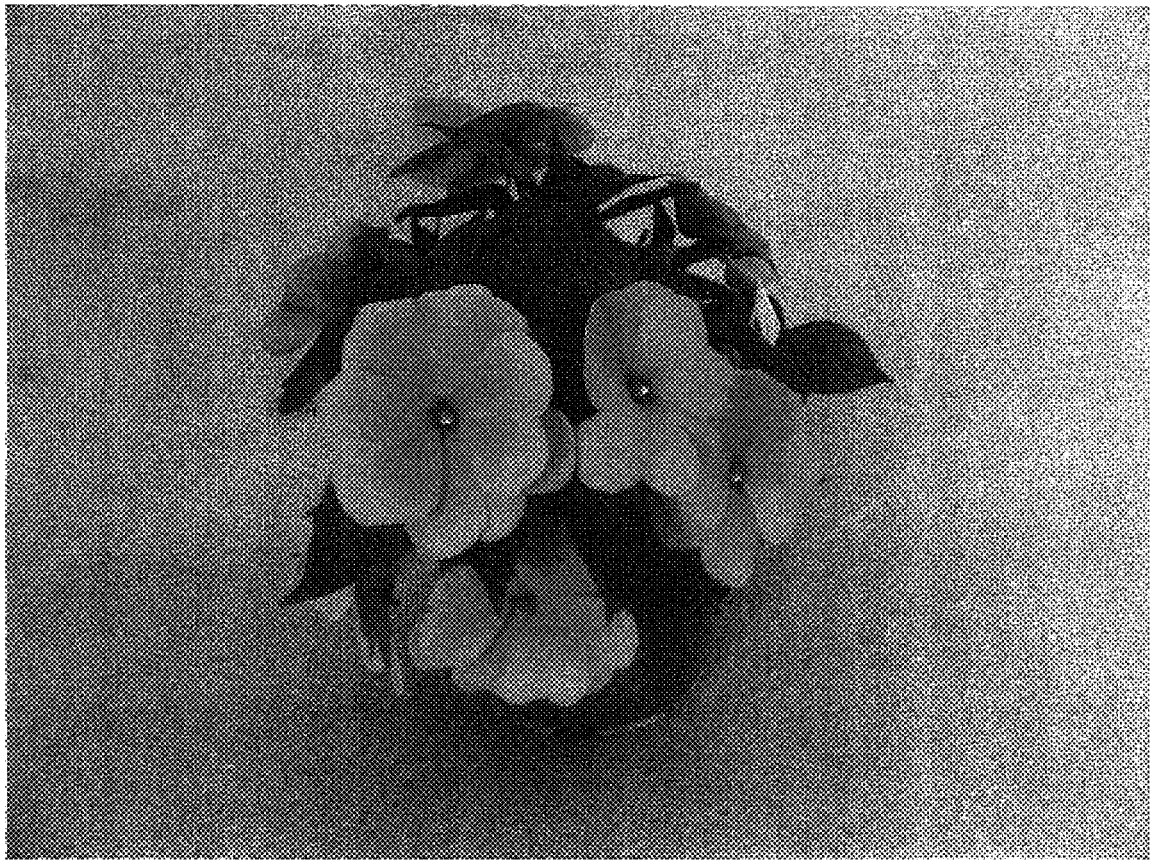

The following detailed description sets forth the characteristics of the new cultivar. The data which defines these characteristics were collected by asexual reproductions carried out in The Netherlands. The color readings were taken indoors in a greenhouse on a sunny day. The new variety was sixteen weeks old from rooting and fully flowering when described. Color references are primarily to The R.H.S. Colour Chart of The Royal Horticultural Society of London (2001).

PLANT

Form: Free and symmetrical.
Height (from soil to top of flowers): 12–16.5 cm.
Plant diameter: 20–25 cm.
Vigor: Upright.
Branching habit: Free.
Lateral branches:
- *Color.*—59B.
- *Texture.*—Smooth.
- *Length.*—9–12 cm.
- *Diameter.*—6–10 mm.
- *Internode length.*—1.2–1.8 cm.
- *Strength.*—Strong.
- *Quantity.*—12–14.

Foliage:
- *Arrangement.*—Primarily in whorls.
- *Number of leaves per stem.*—10–12.
- *Size of leaf.*—Length: 6.8 cm. Width: 2.8 cm.
- *Shape of leaf (generally).*—Lanceolate.
- *Shape of apex.*—Caudate and acuminate.
- *Shape of base.*—Acute.
- *Texture.*—Smooth and rough.
- *Aspect.*—Upward and outward.
- *Margin type.*—Slightly serrated.
- *Fragrance.*—None.
- *Color.*—Young leaves: Upper surface: 139A. Lower surface: 185A. Mature leaves: Upper surface: 139A. Lower surface: 185A.
- *Petiole.*—Length: Young: 5–6 mm. Mature: 10–20 mm. Diameter: Young: 1–2 mm. Mature: 2–3 mm. Color: 59B. Texture: Glabrous.
- *Veins.*—Color: Upper surface: 59B. Lower surface: 59A.

FLOWER

Natural flowering season at specified locations: Usually from March to October, depending on light intensity.

Flower type and habit: Single.
Number of flowers per plant: 18.
Fragrance: None.
Flower height: 8 mm.
Flower diameter: 65 mm.
Bud:
*Shape.*—Ovoid.
*Diameter.*—10 mm.
*Length.*—16 mm.
*Color.*—46A.
Petals:
*Arrangement.*—Whorl.
*Quantity.*—5.
*Length.*—Banner petal: 27 mm. Lateral: 28 mm. Base: 28 mm.
*Width.*—Banner petal: 55 mm. Lateral: 45 mm. Base: 45 mm.
*Shape.*—Cordate.
*Apex.*—Rotundate.
*Base.*—Cuneate.
*Margin.*—Entire.
*Texture.*—Smooth and glabrous.
*Color.*—When opening: Banner petal: Upper surface: 52A with 53C in the middle. Lower surface: 52A with 53C in the middle. Lateral and base petals: Upper surface: 47C. Lower surface: 52B. Fully opened: Banner petals: Upper surface: 52A with 53C in the middle. Lower surface: 52A with 53C in the middle. Lateral and base petals: Upper surface: 47C. Lower surface: 52B.
Spur:
*Quantity.*—1.
*Length.*—50 mm.
*Diameter at apex.*—0.5–1 mm.
*Diameter at flower.*—2 mm.
*Aspect.*—Round.
*Color.*—59A/B.
Peduncles:
*Length.*—2.8–3.8 cm.
*Diameter.*—2.8 mm.
*Color.*—60A.
*Texture.*—Glabrous.
*Orientation.*—Upright.
*Strength.*—Average.
Weather tolerance: +5–+45° C.
Lasting quality:
*On plant.*—3–4 days.
*Of cut flowers.*—1–2 days.
Seed production and description: Not applicable.
Fruit production and description: Not applicable.

REPRODUCTIVE ORGANS

Stamens:
*Number (per flower).*—1.
*Filament length.*—6–8 mm.
*Anthers.*—Shape: Round. Length: 3–4 mm. Color: 58A.
*Pollen.*—Color: 69A/B. Amount: Average.
Pistils:
*Length.*—6–7 mm.
*Styles.*—Length: 1–2 mm. Color: 60B/C.
*Stigma.*—Shape: Round. Color: 60C. Ovary color: 60A.

I claim:

1. A new and distinct variety of New Guinea *impatiens* plant named 'GrüNeu 25' as is herein described and illustrated.

* * * * *

UNITED STATES PATENT AND TRADEMARK OFFICE

CERTIFICATE OF CORRECTION

PATENT NO. : PP 18,260 P2
APPLICATION NO. : 11/480099
DATED : November 27, 2007
INVENTOR(S) : Ralf Schräeder It is certified that error appears in the above-identified patent and that said Letters Patent is hereby corrected as shown below:

Title Page, Item (12) under United States Patent, delete "Schräder" and insert -- Schräeder --.

Title Page, Item (75) Inventor, "Ralf Schräder" should read -- Ralf Schräeder --

Signed and Sealed this

Tenth Day of June, 2008

JON W. DUDAS
*Director of the United States Patent and Trademark Office*